(12) United States Patent
Nagy et al.

(10) Patent No.: US 6,268,309 B1
(45) Date of Patent: Jul. 31, 2001

(54) USE OF A COMPOSITION AND A METHOD FOR THE PROMOTION OF PLANT PRODUCTION AND/OR FOR THE ELIMINATION OF THE UNFAVORABLE INFLUENCES IN PLANT CULTIVATION

(75) Inventors: Péter Literáti Nagy, Budapest; Miklós Kálmán, Szeged, both of (HU)

(73) Assignee: Biorex Kutatóés FejlesztöRt., Budapest (HU)

( * ) Notice: Subject to any disclaimer, the term of this patent is extended or adjusted under 35 U.S.C. 154(b) by 0 days.

(21) Appl. No.: 09/460,310

(22) Filed: Dec. 13, 1999

Related U.S. Application Data

(63) Continuation-in-part of application No. 09/091,808, filed as application No. PCT/HU96/00080 on Dec. 12, 1996, now abandoned.

(30) Foreign Application Priority Data

Dec. 22, 1995 (HU) .................................................. 9503727

(51) Int. Cl.[7] .......................... A01N 33/24; A01N 43/40; A01N 43/74; A01N 43/88
(52) U.S. Cl. .......................... 504/223; 504/244; 504/248; 504/250; 504/251; 504/253
(58) Field of Search ................................... 504/223, 244, 504/248, 250, 251, 253

(56) References Cited

U.S. PATENT DOCUMENTS 4,308,399  12/1981  Takacs et al. ........................ 564/257

FOREIGN PATENT DOCUMENTS

90/04584    5/1990   (WO) .

OTHER PUBLICATIONS

Dormany et al., CA Abstract 123:22821s. Abstract of HU T/66,350.

Kurihara et al., CA Abstract 94:30304. Abstract of "Studies on local anesthetics. XXX. Synthesis and local anesthetic and analgesic activity of the basic derivatives of oximes. II." *Annu. Rep. Tohoku Coll. Pharm.*, 26:83–93.

*Primary Examiner*—S. Mark Clardy
(74) *Attorney, Agent, or Firm*—Heller Ehrman White & McAuliffe LLP

(57) ABSTRACT

Compositions containing hydroximic acid derivatives of the formula

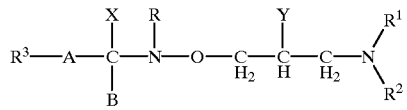

where $R^1$, $R^2$, $R^3$, R, X, Y, A, and B are as defined in the specification, are useful for the promotion of plant production and/or for the elimination of unfavourable environmental influences in plant cultivation.

20 Claims, No Drawings

USE OF A COMPOSITION AND A METHOD FOR THE PROMOTION OF PLANT PRODUCTION AND/OR FOR THE ELIMINATION OF THE UNFAVORABLE INFLUENCES IN PLANT CULTIVATION

This application is a CIP of Ser. No. 09/091,808, filed Jan. 12, 1999, abandoned which had been filed under 35 USC 371 as the national stage application of international application PCT/HU96/00080, filed Dec. 12, 1996

The invention refers to the use of a composition and a method for the promotion of plant production and/or for the elimination of the unfavourable environmental influences in plant cultivation.

More specifically, the invention refers to the use of a composition comprising a hydroximic acid derivative of the formula

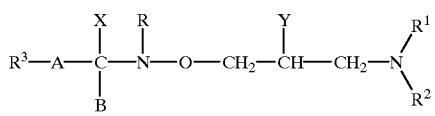

I wherein
$R^1$ represents a hydrogen atom or a $C_{1-5}$ alkyl group,
$R^2$ stands for a hydrogen atom, a $C_{1-5}$ alkyl group, a $C_{3-8}$ cycloalkyl group or a phenyl group optionally substituted by a hydroxy or a phenyl group, or
$R^1$ and $R^2$ together with the nitrogen atom they are attached to form a 5 to 8 membered ring optionally containing on or more further nitrogen, oxygen or sulfur atom(s) and said ring can be condensed with another alicyclic or heterocyclic ring, preferably a benzene, naphthalene, quinoline, isoquinoline, pyridine or pyrazoline ring, furthermore, if desired and chemically possible, the nitrogen and/or sulfur heteroatom(s) are present in the form of an oxide or dioxide,
$R^3$ means a hydrogen atom, a phenyl group, a naphthyl group or a pyridyl group wherein said groups can be substituted by one or more halo atom(s) or $C_{1-4}$ alkoxy group(s),
Y is a hydrogen atom, a hydroxy group, a $C_{1-24}$ alkoxy group optionally substituted by an amino group, a $C_{2-24}$ polyalkenyloxy group containing 1 to 6 double bond(s), a $C_{1-25}$ alkanoyl group, a $C_{3-9}$ alkenoyl group or a group of the formula $R^7$—COO— wherein $R^7$ represents a $C_{2-30}$ polyalkenyl group containing 1 to 6 double bond(s),
X stands for a halo atom, an amino group, a $C_{1-4}$ alkoxy group, or
X forms with B an oxygen atom, or
X and Y together withv the carbon atoms they are attached to and the —NR—O—CH$_2$— group being between said carbon atoms form a ring of the formula

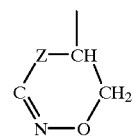

a wherein z represents an oxygen atom or a nitrogen atom,
R stands for a hydrogen atom or
R forms with B a chemical bond,
A is a $C_{1-4}$ alkylene group or a chemical bond or a group of the formula

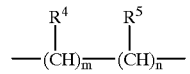

b wherein
$R^4$ represents a hydrogen atom, a $C_{1-5}$ alkyl group, a $C_{3-8}$ cycloalkyl group or a phenyl group optionally substituted by a halo atom, a $C_{1-4}$ alkoxy group or a $C_{1-5}$ alkyl group,
$R^5$ stands for a hydrogen atom, a $C_{1-4}$ alkyl group or a phenyl group,
m has a value of 0, 1 or 2
n has a value of 0, 1 or 2,
with the proviso that Y is other than hydroxy when X is an amino group,
or a physiologically acceptable acid addition salt thereof as the active ingredient.

The hydroximic acid derivatives of the formula I are known.

U.S. Pat. No. 4,308,399 describes hydroximic acid derivatives within the compounds of the formula I suitable for the treatment of diabetic angiopathy.

EP No. 417 210 also describes hydroximic acid halides within the formula I having a selective beta-blocking effect, thus, being suitable for the treatment of diabetic angiopathy.

HU-P Application No. 2385/92 published under No. T/66350 describes further hydroximic acid derivatives within the formula I. These known compounds can be used in the treatment of vascular deformations, mainly in the therapy of diabetes mellitus.

Plants have a very important role from the point of view of the life on the earth. They are nutrient source for the animal world including man, and they have a considerable part in the preparation of oxygen that is essential for the life.

For the optimal growth and production conditions of plants they have to be adaptable to the environmental conditions. If these environmental factors are suddenly changed in a drastic manner (e.g. due to a long-lasting drought, a sudden cooling down to about 0° C. or the appearance of acidic, mutagenic or radiating agents in the environment), then the fertility and in many cases even the surviving ability of plants are significantly reduced.

The plants are especially sensitive to these sudden unfavourable changes in the germinating state since their natural defensive ability i.e. a certain buffering ability have not developed yet to a sufficient extent.

Thus, there is a need to find substances having low or high molecular weight which could enhance the natural defensive mechanisms of plants to increase the survival chances thereof in case of extreme environmental changes.

Presumably, such substances should have general properties that promote the maintenance or regeneration of the biological integrity of plant cell membranes. Furthermore, such substances should be able to induce the defensive mechanisms of plant cells, thus, avoiding the irreversible damage of the chromosome set or the mitochondrial genom of the cell.

Owing to substances having the above properties plants could probably tolerate the detrimental effects of chemical or mutagenic agents that appear in the environment.

If, by means of such substances, plants are able to tolerate the low water concentration of the cells for a longer time, then also lands having a restricted water supply could be cultivated.

If the germinating seeds could be made resistant to low temperature or they could tolerate cooling down to a temperature below freezing point for a limited time, then certain domesticated plants could be sowed sooner, on the one part, and the crop land there of could be shifted to northern areas, on the other. In both cases a considerable economical benefit can be expected.

It was found that the above need is fulfilled by the use of a composition of the invention comprising a hydroximic acid derivative of the formula I or a physiologically acceptable acid addition salt thereof as the active ingredient.

Thus, the composition used according to the invention comprises a hydroximic acid derivative of the formula I or a physiologically acceptable acid addition salt thereof as the active ingredient in admixture with one or more conventional solid or liquid carrier(s) of compositions used in plant protection.

In the specification and claims a $C_{1-5}$ alkyl group is, for example, a methyl, ethyl, n-propyl, isopropyl, n-butyl or n-pentyl group, peferably a methyl or an ethyl group.

A $C_{3-8}$ cycloalkyl. group is, for example, a cyclopropyl, cyclopentyl, cyclohexyl, cycloheptyl or cyclooctyl group, preferably a cyclopentyl or a cyclohexyl group.

A 5 to 8 membered ring containing one or more heteroatom(s) can be, for example, a pyrrole, pyrazole, imidazole, oxazole, thiazole, pyridine, pyridazine, pyrirmidine, piperazine, morpholine, indole, quinoline etc. ring.

A $C_{1-24}$ alkoxy group is, for example, a methoxy, ethoxy, n-propoxy, tert.-butoxy, n-pentoxy, decyloxy, dodecyloxy, octadecyloxy etc. group.

A $C_{1-25}$ alkanoyl group is, for example, a formyl, acetyl, propionyl, butiryl, caproyl, palmityl, stearyl etc. group.

A $C_{3-9}$ alkenoyl group is, for example, an acryloyl, pentenoyl, hexenoyl, heptenoyl, octenoyl etc. group.

A $C_{1-4}$ alkylene group is, for example, a methylene, ethylene, propylene or butylene group.

A halo atom is, for example, a fluoro, chloro, bromo or iodo atom, preferably a chloro or a bromo atom.

If Y stands for a group of the formula $R^7$—COO—, it can represent, for example, a linolenoyl, linoloyl, docosahexanoyl, eicosapentanoyl, arachidonoyl etc. group.

The physiologically acceptable acid addition salts of the compounds of the formula I are the acid addition salts formed with physiologically acceptable inorganic acids such as hydrochloric acid, sulfuric acid etc. or with physiologically acceptable organic acids such as acetic acid, fumaric acid, lactic acid etc.

A preferred subgroup of the compounds of the formula I consists of the hydroximic acid derivatives of the formula

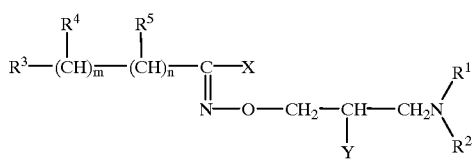

II wherein $R^1$, $R^2$, $R^3$, $R^4$, $R^5$, m and n are as stated in relation to formula I, X represents a halo atom or an amino group, Y means a hydroxy group,
with the proviso that Y is other than hydroxy when X is an amino group.

Especially preferred compounds of the formula II are those wherein $R^1$ and $R^2$ together wiih the nitrogen atom they are attached to form a piperidino group, $R^3$ stands for a pyridyl group, m and n have a value of 0, X is as defined above. Of these compounds, preferred species are as follows:

N-/2-hydroxy-3-(peperidinyl)propoxy/-3-pyridinecarboximidoyl chloride.

A further preferred subgroup of the hydroximic acid derivatives of the formula I consists of the compounds of the formula

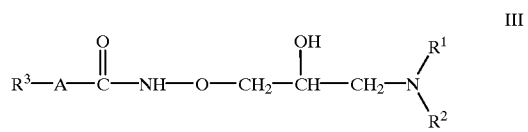

III wherein $R^1$, $R^2$, $R^3$ and A are as stated in relation to formula I.

Another preferred subgroup of the hydroximid acid derivatives of the formula I consists of the compound of the formula

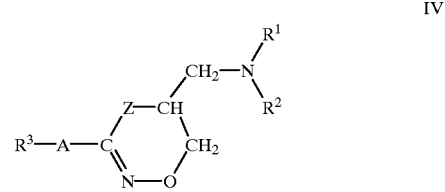

IV wherein $R^1$, $R^2$, $R^3$ and A are as stated in relation to formula I, Z represents an oxygen or a nitrogen atom.

A still further preferred subgroup of the hydroximic acid derivatives of the formula I consists of the compounds of the formula

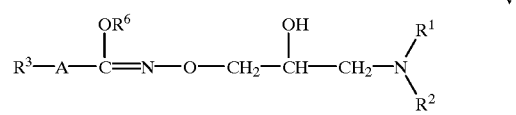

V wherein $R^1$, $R^2$, $R^3$ and A are as stated in relation to formula I, $R^6$ stands for a $C_{1-4}$ alkyl group.

The compounds of the formula I can be prepared by the processes known from HU-P Nos. 177 578 and 207 988 as well as from HU-P Application published under No. T/66350.

The composition used according to the invention contains 0.01 to 95% by weight, preferably 0.1 to 20% by weight of a hydroximic acid derivative of the formula I or a physiologically acceptable acid addition salt thereof as the active ingredient in admixture with one or more conventional solid or liquid carrier(s) of compositions used in plant protection.

The composition used according to the invention can be solid or liquid, thus a powder mixture, solution, suspension, emulsion etc.

Essentially, any type of the compositions employed in plant protection may contain the active ingredient of the formula I.

Correspondingly, the carrier can be a solvent such as water, ethylene glycol, propylene glycol, glycerol, poly (ethylene glycol), vegetable oil, mineral oil etc.; a surface active agent such as an ionic or nonionic emulgator; a conventional agent used in cultivation for amelioriation work such as powdered limestone, powdered dolomite, perlite grist, fertilizer, mineral salt, microelement, plant protective agent such as fungicide etc.

Suitably, the composition used according to the invention is diluted with water before use, and in general the solution, suspension or emulsion containing 0.0001 to 1.0% by weight of the compound of the formula I is employed for the treatment or leaf or root thereof is contacted with the compound of the formula I or a physiologically acceptable acid addition salt thereof and a solution, suspension or emulsion containing said compound, respectively.

For example, the seed of the plant to be cultivated can be treated with a seed-dressing composition comprising a compound of the formula I, or a seedling of the plant can be sprayed with a solution, suspension or emulsion comprising a compound of the formula I.

The plant cultivated or the leaves thereof can be contacted through spraying with a solution, suspension or emulsion of a compound of the formula I, or the soil around the roots can be sprinkled with said solution, suspension or emulsion.

A further possibility of treatment consists of adding a concentrated or diluted form of the composition of the invention to the spray used during the conventional plant protection work to obtain a final spray containing the compound of the formula I in the required concentration. In this way,. the treatment of the invention is performed together with the conventional plant protection treatment.

Thus, a further embodiment of the invention consists of a method for the promotion of plant production and/or for the elimination of the unfavourable environmental influences in plant cultivation. According to the method of the invention, the plant to be cultivated or a seed or seedling or leaf or root thereof is treated with an effective non-toxic amount of a hydroximic acid derivative of the formula I or a physiologically acceptable acid addition salt thereof.

Preferably, the plant to be cultivated or a seed or seedling or leaf or root thereof is treated with a composition comprising 0.0001 to 1.0% by weight of a compound of the formula I or a physiologically acceptable acid addition salt thereof in admixture with one or more conventional solid or liquid carrier(s) of compositions used in plant protection.

Under the term "unfavourable environmental influences" for example nutrient deficiency, stress, the presence of heavy metal salts in the soil, and/or too cold or too warm environment etc. are meant. If seeds treated with a compound of the formula I are used for the cultivation, the plants are treated once or several times with a solution, suspension or emulsion of a compound of the formula I, the growth of the plants resist to the unfavourable environmental influences.

The compositon and method of the invention can be preferably used in the cultivation of plants such as maize, bean, muscat melon, sunflower, tomato, capsicum, white mustard, poppy, amaranth, pigeon-berry, apricot, peach etc.

The effect of the compounds of the formula I on the plant cultivation was studied as given below:

In the experiments the following active ingredient was used: compound "A":

N-/2-hydroxy-3-(piperidinyl)propoxy/-3-pyridinecarboximidoyl chloride malate.

1. Study of Frost Resistance on Maize

For the investigation of the frost resistance, the surface of the maize seeeds was treated with the aqueous solutions of the active ingredients. The concentration of the solutions used were: 1 g/l; 0.1 g/l; 0.01 g/l; and 0.001 g/l. After the treatment the seeds were placed onto a filter paper and let to germinate by adding the required amount of water at a uniform ratio. Then the seeds, germinated or not, were implanted into normal mould placed in plastic flacons. 20 ml of tap water were added to each flacon day by day. 14 to 15 days after the treatment of the seeds the plastic flacons were placed into a freezer (Zanussi, 50 litres) and left there for the indicated time at −17° C. Then the flacons were removed, the freezer was left to cool down to −17° C., and further plastic flacons were placed into it taking care that always the same mass of flacons should be placed in.

The number of experiments that could be performed was highly restricted by the fact that the natural Yearly biorythm of the plants must be followed. In case of a deviation from the biorythm exceeding a month, the results obtained cannot be compared with plants grown on free land.

The germination ratio of maize seeds was equivalent to nearly 100%, thus it is not indicated in detail.

1.1 Frost Treatment in Function of Time

To study the effect of compound "A" always 50 pieces of maize seeds were treated with a solution thereof having the same concentration. Then the seeds were divided into groups consisting of 10 to 11 pieces. One group of the germinated and implanted seeds were subjected to frost treatment for 10 minutes, another group of the germinated and implanted seeds were subjected to frost treatment for 15 minutes and a further group of the germinated and implanted seeds were subjected to frost treatment for 20 minutes. The ratio (in percentage) of the surviving plants is given in Table I in case of the treatment with a 0.01 g/l solution of compound "A". In the control group the maize seeds were treated with water.

TABLE I

| Seed | Number of seeds | | |
|---|---|---|---|
| group | treated | damaged | Survival in % |
| Treatment at −17° C. for 10 minutes | | | |
| control | 11 | 9 | 18.18 |
| test | 10 | 4 | 60.00 |
| Treatment at −17° C. for 15 minutes | | | |
| control | 10 | 7 | 30.00 |
| test | 11 | 1 | 90.91 |
| Treatment at −17° C. for 20 minutes | | | |
| control | 10 | 8 | 20.00 |
| test | 10 | 1 | 90.00 |

From Table I it can be seen that compound "A" can protect the plant at a concentration of 0.01 g/l from freezing even in a frost treatment lasting for 20 minutes. The effective dose for a seed amaounts to 0.182 mcg.

1.2 Survival of Maize after a 10 Minutes' Frost Treatment

The maize plants having 3 to 4 leaves grown from the seeds treated with the aqueous solutions of compound "A" were subjected to the frost treatment at −17° C. for 10 minutes. The study simulated the physiological state when maize plants were endangered by early frosts in April. The results of the survival tests are summarized in Table II.

TABLE II

| Conc. of compound | Number of plants | | | |
|---|---|---|---|---|
| "A" in g/l | unharmed | damaged | total | Survival in % |
| 1.0 | 24 | 5 | 29 | 82.70 |
| 0.1 | 22 | 7 | 29 | 75.80 |
| 0.01 | 20 | 7 | 27 | 74.10 |
| 0.001 | 22 | 5 | 27 | 81.50 |

From Table II it can be seen that an excellent frost resistance is obtained in case of a treatment with compound "A" even at a solution concentration of 0.001 g/l.

2. Study of the Promotion of Plant Growth

The maize plants obtained from the seeds treated with aqueous solutions of compound "A" of different concentrations were grown and the height of each plant as well as the average height was determined on day 11 and 14, respectively. The control group was treated with water. The results obtained are shown in Tables III and IV,

TABLE III

Height of maize treated with compound "A" after 11 days

| Height (in cm) of plants treated with compound "A" in g/l solution | | | | |
|---|---|---|---|---|
| 1.0 | 0.1 | 0.01 | 0.001 | Control |
| 26 | 62 | 56 | 140 | 1 |
| 64 | 23 | 30 | 119 | 3 |
| 46 | 73 | 50 | 105 | 2 |
| 109 | 22 | 54 | 76 | 1 |
| 62 | 64 | 22 | 76 | 3 |
| 50 | 60 | 40 | 80 | 4 |
| 40 | 61 | 36 | 107 | 2 |
| 79 | 82 | 10 | 33 | 1 |
| 61 | 31 | 22 | 114 | 1 |
| 58 | 34 | 77 | 166 | 3 |
| 66 | 41 | 40 | 30 | 3 |
| 58 | 88 | 56 | 53 | 1 |
| 52 | 67 | 88 | 39 | 3 |
| 42 | 67 | 66 | 42 | 2 |
| 75 | 54 | 40 | 15 | 1 |
| 48 | 67 | 27 | 42 | 1 |
| 42 | 29 | 33 | 9 | 1 |
| 33 | 33 | 43 | 76 | 3 |
| 69 | 42 | 18 | 36 | 1 |
| 67 | 40 | 58 | 17 | 1 |
| 56 | 58 | 54 | 72 | 2 |
| 54 | 28 | 52 | 43 | 2 |
| 65 | 12 | — | 47 | 1 |
| 30 | 63 | — | 67 | 2 |
| 33 | 57 | — | 82 | 2 |
| 10 | 50 | — | 16 | 1 |
| — | — | — | 11 | 2 |
| — | — | — | — | 1 |
| — | — | — | — | 1 |
| Number of plants 26 | 26 | 22 | 27 | 29 |
| Average height 53.7 | 50.3 | 44.2 | 63.4 | 1.8 |

TABLE IV

Height of maize treated with compound "A" after 14 days

| Height (in cm) of plants treated with compound "A" in g/l solution | | | | |
|---|---|---|---|---|
| 1.0 | 0.1 | 0.01 | 0.001 | Control |
| 147 | 110 | 156 | 140 | 45 |
| 172 | 130 | 72 | 119 | 12 |
| 190 | 28 | 85 | 105 | 18 |
| 75 | 78 | 155 | 76 | 22 |
| 109 | 109 | 153 | 76 | 37 |
| 77 | 101 | 18 | 80 | 16 |
| 47 | 63 | 28 | 107 | 29 |
| 108 | 146 | 64 | 33 | 24 |
| 84 | 152 | 90 | 114 | 35 |
| 74 | 156 | 93 | 166 | 16 |
| 109 | 54 | 69 | 30 | 49 |
| 142 | 159 | 34 | 53 | 18 |
| 8 | 175 | 50 | 39 | 23 |
| 6 | 97 | 83 | 42 | 36 |
| 18 | 111 | 106 | 15 | 25 |
| 160 | 145 | 85 | 42 | 14 |
| 221 | 163 | 135 | 9 | 38 |
| 97 | 70 | 141 | 76 | 43 |
| 129 | 146 | 111 | 36 | 11 |
| 75 | 38 | 176 | 17 | 39 |

TABLE IV-continued

Height of maize treated with compound "A" after 14 days

| Height (in cm) of plants treated with compound "A" in g/l solution | | | | |
|---|---|---|---|---|
| 1.0 | 0.1 | 0.01 | 0.001 | Control |
| 125 | 108 | 173 | 72 | 28 |
| 102 | 24 | 120 | 43 | 12 |
| 187 | 139 | 168 | 47 | 44 |
| 141 | 168 | 101 | 67 | 53 |
| 155 | 153 | 43 | 82 | 17 |
| 150 | 135 | 98 | 16 | 10 |
| 146 | 204 | 70 | 11 | 39 |
| 110 | 112 | — | — | 41 |
| 75 | 124 | — | — | 32 |
| Number of plants 29 | 29 | 27 | 27 | 29 |
| Average height 111.7 | 117.2 | 99.1 | 63.4 | 28.5 |

From Tables III an IV it can be seen that the method of the invention exerts a positive effect on the growing of the plants. In case of the control groups, the average height is very low on day 11, and even on day 14, the control plants are considerably less developed than the plants treated according to the invention.

It is to be mentioned that in an experiment maize plants grown from untreated seeds were sprayed with a solution of compound "A" of optimum concentration in the 3 weeks' state, and on the next day the plants were subjected to a frost treatment. In some hours the 15 plants examined were destroyed.

The above experiments prove that the composition of the invention is indeed suitable for the promotion of plant production and for the elimination of the unfavourable enrivonmental influences in plant cultivation.

We claim:

1. A composition for the promotion of plant production and/or for the elimination of unfavorable environmental influences in plant cultivation comprising:

a hydroximic acid derivative of the formula

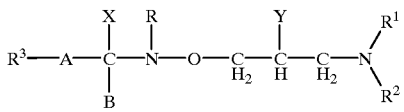

where $R^1$ is a hydrogen atom or a $C_{1-5}$ alkyl group, $R^2$ is a hydrogen atom, a $C_{1-5}$ alkyl group, a $C_{3-8}$ cycloalkyl group, or a phenyl group optionally substituted with a hydroxy or a phenyl group, or $R^1$ and $R^2$ together with the nitrogen atom to which they are attached form a 5- to 8-membered ring optionally containing one or more further nitrogen, oxygen, or sulfur atoms, the ring being optionally condensed with another alicyclic or heterocyclic ring, and the nitrogen and/or sulfur atoms being optionally present in the form of an oxide or dioxide, $R^3$ is a hydrogen atom, a phenyl group, a naphthyl group, or a pyridyl group, each of these groups being optionally substituted with one or more halo atoms or $C_{1-4}$ alkoxy groups, Y is a hydrogen atom, a hydroxy group, a $C_{1-24}$ alkoxy group optionally substituted with an amino group, a $C_{2-24}$ polyalkenyloxy group containing 1 to 6 double bonds, a $C_{1-25}$ alkanoyl group, a $C_{3-9}$ alkenoyl group, or a group of the formula $R^7COO-$ where $R^7$ is a $C_{2-30}$ polyalkenyl group containing 1 to 6 double bonds, X is a halo atom, an amino group, or a $C_{1-4}$ alkoxy group, except that X is not an amino group if Y is a hydroxy group, or X and B together are an oxygen atom, or X and Y together with the carbon atoms to which they are attached and the —NR—O—CH₂— group between these carbon atoms form a ring of the formula

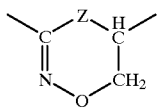

where Z is an oxygen atom or a nitrogen atom,
R is a hydrogen atom, or
R and B together are a chemical bond,
A is a $C_{1-4}$ alkylene group, a chemical bond, or a group of the formula

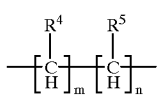

where
$R^4$ is a hydrogen atom, a $C_{1-5}$ alkyl group, a $C_{3-8}$ cycloalkyl group, or a phenyl group optionally substituted by a halo atom, a $C_{1-4}$ alkoxy group, or a $C_{1-5}$ alkyl group,
$R^5$ is a hydrogen atom, a $C_{1-4}$ alkyl group, or a phenyl group,
m is 0, 1, or 2, and
n is 0, 1, or 2,
or a physiologically acceptable acid addition salt thereof, as the active ingredient,
in admixture with at least one conventional solid or liquid carrier of compositions used in plant protection.

2. A composition of claim 1 in which the hydroximic acid derivative is a compound of the formula

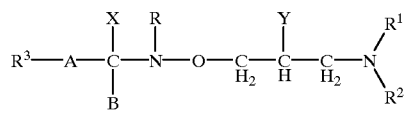

where
$R^1$ and $R^2$ together with the nitrogen atom to which they are attached form a 5- to 8-membered ring optionally containing one or more further nitrogen, oxygen, or sulfur atoms, the ring being condensed with a benzene, naphthalene, quinoline, isoquinoline, pyridine, or pyrazoline ring, the nitrogen and/or sulfur atoms being optionally present in the form of an oxide or dioxide,
$R^3$, R, X, Y, A, and B are as defined in claim 1,
or a physiologically acceptable acid addition salt thereof.

3. A composition of claim 1 in which the hydroximic acid derivative is a compound of the formula

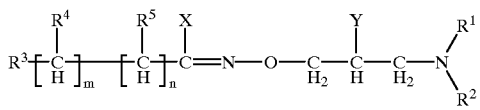

where $R^1$, $R^2$, $R^3$, $R^4$, $R^5$, m, and n are as defined in claim 1,
X is a halo atom or an amino group, and
Y is a hydroxy group,
or a physiologically acceptable acid addition salt thereof.

4. A composition of claim 1 in which the hydroximic acid derivative is a compound of the formula

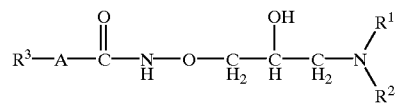

where
$R^1$, $R^2$, $R^3$, and A are as defined in claim 1,
or a physiologically acceptable acid addition salt thereof.

5. A composition of claim 1 in which the hydroximic acid derivative is a compound of the formula

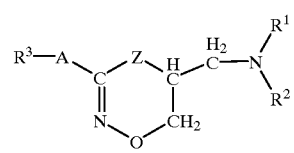

where
$R^1$, $R^2$, $R^3$, and A are as defined in claim 1, and
Z is an oxygen atom or a nitrogen atom,
or a physiologically acceptable acid addition salt thereof.

6. A composition of claim 1 in which the hydroximic acid derivative is a compound of the formula

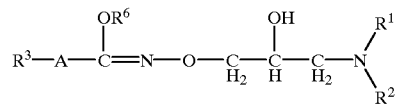

where
$R^1$, $R^2$, $R^3$, and A are as defined in claim 1, and
$R^6$ is a $C_{1-4}$ alkyl group,
or a physiologically acceptable acid addition salt thereof.

7. A composition of claim 3 in which the hydroximic acid derivative is a compound of the formula

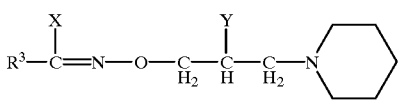

where
$R^3$, X, and Y are as defined in claim 3,
or a physiologically acceptable acid addition salt thereof.

8. The composition of claim 7 in which the hydroximic acid derivative is N-[2-hydroxy-3-(1-piperidinyl)propoxy]-3-pyridine-carboximidoyl chloride or a physiologically acceptable acid addition salt thereof.

9. A composition for the treatment of a plant to be cultivated or a seed, seedling, leaf, or root thereof for the promotion of plant production and/or for the elimination of unfavorable environmental influences in plant cultivation comprising:
an effective non-toxic amount from 0.0001% to 1.0% by mass of the composition of a hydroximic acid derivative of the formula

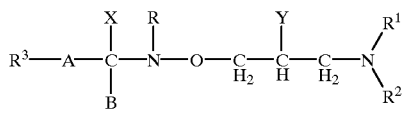

where
- $R^1$ is a hydrogen atom or a $C_{1-5}$ alkyl group,
- $R^2$ is a hydrogen atom, a $C_{1-5}$ alkyl group, a $C_{3-8}$ cycloalkyl group, or a phenyl group optionally substituted with a hydroxy or a phenyl group, or
- $R^1$ and $R^2$ together with the nitrogen atom to which they are attached form a 5- to 8-membered ring optionally containing one or more further nitrogen, oxygen, or sulfur atoms, the ring being optionally condensed with another alicyclic or heterocyclic ring, and the nitrogen and/or sulfur atoms being optionally present in the form of an oxide or dioxide,
- $R^3$ is a hydrogen atom, a phenyl group, a naphthyl group, or a pyridyl group, each of these groups being optionally substituted with one or more halo atoms or $C_{1-4}$ alkoxy groups,
- Y is a hydrogen atom, a hydroxy group, a $C_{1-24}$ alkoxy group optionally substituted with an amino group, a $C_{2-24}$ polyalkenyloxy group containing 1 to 6 double bonds, a $C_{1-25}$ alkanoyl group, a $C_{3-9}$ alkenoyl group, or a group of the formula $R^7COO$— where $R^7$ is a $C_{2-30}$ polyalkenyl group containing 1 to 6 double bonds,
- X is a halo atom, an amino group, or a $C_{1-4}$ alkoxy group, except that X is not an amino group when Y is a hydroxy group, or
- X and B together are an oxygen atom, or
- X and Y together with the carbon atoms to which they are attached and the —NR—O—CH$_2$— group between these carbon atoms form a ring of the formula

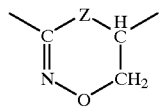

where Z is an oxygen atom or a nitrogen atom,
- R is a hydrogen atom, or
- R and B together are a chemical bond,
- A is a $C_{1-4}$ alkylene group, a chemical bond, or a group of the formula

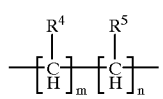

where
- $R^4$ is a hydrogen atom, a $C_{1-5}$ alkyl group, a $C_{3-8}$ cycloalkyl group, or a phenyl group optionally substituted by a halo atom, a $C_{1-4}$ alkoxy group, or a $C_{1-5}$ alkyl group,
- $R^5$ is a hydrogen atom, a $C_{1-4}$ alkyl group, or a phenyl group,
- m is 0, 1, or 2, and
- n is 0, 1, or 2, or a physiologically acceptable acid addition salt thereof, as the active ingredient,
in admixture with at least one conventional solid or liquid carrier of compositions used in plant protection.

10. A composition of claim 9 in which the hydroximic acid derivative is a compound of the formula

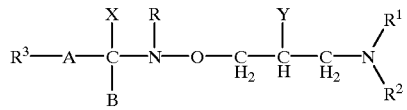

where
- $R^1$ and $R^2$ together with the nitrogen atom to which they are attached form a 5- to 8-membered ring optionally containing one or more further nitrogen, oxygen, or sulfur atoms, the ring being condensed with a benzene, naphthalene, quinoline, isoquinoline, pyridine, or pyrazoline ring, the nitrogen and/or sulfur atoms being optionally present in the form of an oxide or dioxide,
- $R^3$, R, X, Y, A, and B are as defined in claim 9, or a physiologically acceptable acid addition salt thereof.

11. A composition of claim 9 in which the hydroximic acid derivative is a compound of the formula

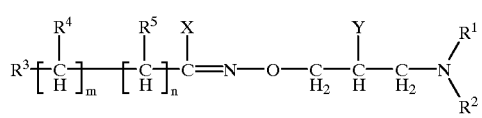

where
- $R^1$, $R^2$, $R^3$, $R^4$, $R^5$, m, and n are as defined in claim 9,
- X is a halogen atom or an amino group, and
- Y is a hydroxy group, or a physiologically acceptable acid addition salt thereof.

12. A composition of claim 9 in which the hydroximic acid derivative is a compound of the formula

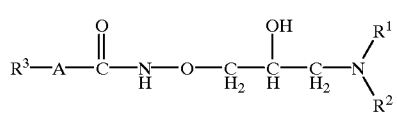

where
- $R^1$, $R^2$, $R^3$, and A are as defined in claim 9, or a physiologically acceptable acid addition salt thereof.

13. A composition of claim 9 in which the hydroximic acid derivative is a compound of the formula

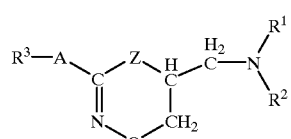

where
- $R^1$, $R^2$, $R^3$, and A are as defined in claim 9, and
- Z is an oxygen atom or a nitrogen atom, or a physiologically acceptable acid addition salt thereof.

14. A composition of claim 9 in which the hydroximic acid derivative is a compound of the formula

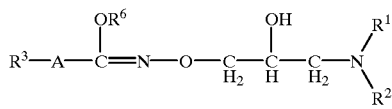

where
$R^1$, $R^2$, $R^3$, and A are as defined in claim 9, and
$R_6$ is a $C_{1-4}$ alkyl group,
or a physiologically acceptable acid addition salt thereof.

15. A composition of claim 11 in which the hydroximic acid derivative is a compound of the formula

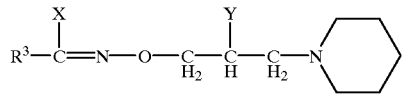

where
$R^3$, X, and Y are as defined in claim 11,
or a physiologically acceptable acid addition salt thereof.

16. The composition of claim 15 in which the hydroximic acid derivative is N-[2-hydroxy-3-(1-piperidinyl)propoxy]-3-pyridine-carboximidoyl chloride or a physiologically acceptable acid addition salt thereof.

17. A method for the promotion of plant production and/or for the elimination of unfavorable environmental influences in plant cultivation comprising treatment of a plant to be cultivated or a seed, seedling, leaf, or root thereof with an effective non-toxic amount of a hydroximic acid derivative of the formula

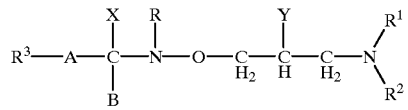

where
$R^1$ is a hydrogen atom or a $C_{1-5}$ alkyl group,
$R^2$ is a hydrogen atom, a $C_{1-5}$ alkyl group, a $C_{3-8}$ cycloalkyl group, or a phenyl group optionally substituted with a hydroxy or a phenyl group, or
$R^1$ and $R^2$ together with the nitrogen atom to which they are attached form a 5- to 8-membered ring optionally containing one or more further nitrogen, oxygen, or sulfur atoms, the ring being optionally condensed with another alicyclic or heterocyclic ring, and the nitrogen and/or sulfur atoms being optionally present in the form of an oxide or dioxide,
$R^3$ is a hydrogen atom, a phenyl group, a naphthyl group, or a pyridyl group, each of these groups being optionally substituted with one or more halo atoms or $C_{1-4}$ alkoxy groups,
Y is a hydrogen atom, a hydroxy group, a $C_{1-24}$ alkoxy group optionally substituted with an amino group, a $C_{2-24}$ polyalkenyloxy group containing 1 to 6 double bonds, a $C_{1-25}$ alkanoyl group, a $C_{3-9}$ alkenoyl group, or a group of the formula $R^7COO-$ where $R^7$ is a $C_{2-30}$ polyalkenyl group containing 1 to 6 double bonds, X is a halo atom, an amino group, or a $C_{1-4}$ alkoxy group, except that X is not an amino group when Y is a hydroxy group, or
X and B together are an oxygen atom, or
X and Y together with the carbon atoms to which they are attached and the $-NR-O-CH_2-$ group between these carbon atoms form a ring of the formula

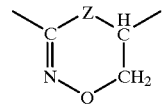

where Z is an oxygen atom or a nitrogen atom,
R is a hydrogen atom, or
R and B together are a chemical bond,
A is a $C_{1-4}$ alkylene group, a chemical bond, or a group of the formula

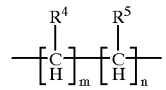

where
$R^4$ is a hydrogen atom, a $C_{1-5}$ alkyl group, a $C_{3-8}$ cycloalkyl group, or a phenyl group optionally substituted by a halo atom, a $C_{1-4}$ alkoxy group, or a $C_{1-5}$ alkyl group,
$R^5$ is a hydrogen atom, a $C_{1-4}$ alkyl group, or a phenyl group,
m is 0, 1, or 2, and
n is 0, 1, or 2,
or a physiologically acceptable acid addition salt thereof.

18. The method of claim 17 in which the treatment comprises administration of a composition comprising 0.0001% to 1.0% by mass of the composition of the hydroximic acid derivative or a physiologically acceptable acid addition salt thereof.

19. The method of claim 17 in which the hydroximic acid derivative is a compound of the formula

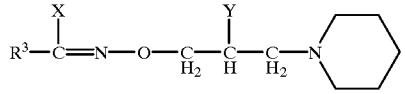

where
$R^3$ is as defined in claim 17,
X is a halo atom or an amino group, and
Y is a hydroxy group,
or a physiologically acceptable acid addition salt thereof.

20. The method of claim 19 in which the hydroximic acid derivative is N-[2-hydroxy-3-(1-piperidinyl)propoxy]-3-pyridine-carboximidoyl chloride or a physiologically acceptable acid addition salt thereof.

* * * * *